United States Patent
Itoh

(12) 
(10) Patent No.: US 6,587,712 B1
(45) Date of Patent: Jul. 1, 2003

(54) PORTABLE ELECTROCARDIOGRAM MONITOR

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 0 days.

(21) Appl. No.: 09/579,042

(22) Filed: May 26, 2000

(30) Foreign Application Priority Data

May 31, 1999 (JP) .......................... 11-152472
May 8, 2000 (JP) ....................... 2000-134704

(51) Int. Cl.⁷ .......................................... A61B 5/0402
(52) U.S. Cl. ..................................... 600/515; 600/509
(58) Field of Search .................... 600/509, 515, 600/523; 128/923

(56) References Cited

U.S. PATENT DOCUMENTS

| | | | | |
|---|---|---|---|---|
| 4,457,315 A | * | 7/1984 | Bennish ...................... | 600/517 |
| 4,546,776 A | * | 10/1985 | Bellin et al. ................ | 600/517 |
| 5,033,475 A | | 7/1991 | Ueda et al. | |
| 5,289,824 A | * | 3/1994 | Mills et al. ................. | 128/904 |
| 5,483,967 A | * | 1/1996 | Ohtake ....................... | 128/903 |

FOREIGN PATENT DOCUMENTS

| | | |
|---|---|---|
| JP | 1148236 | 7/1987 |
| JP | 1305926 | 12/1989 |
| JP | 5123302 | 5/1993 |
| JP | 9262217 | 10/1997 |

* cited by examiner

*Primary Examiner*—Kennedy Schaetzle
(74) *Attorney, Agent, or Firm*—Volpe and Koenig, P.C.

(57) ABSTRACT

A portable electrocardiogram monitor according to the present invention includes an electrode piece fixed in contact with the surface of a body of a user, for receiving an electrical signal corresponding to a bioelectric current generated by contraction of heart muscles, a signal amplifier for amplifying the electrical signal, a processor for processing the amplified signal to acquire electrocardiogram waveform data, a display for displaying an electrocardiogram based on the electrocardiogram waveform data, a memory for storing electrocardiogram waveform data of the user who is in good health, as standard data, a comparator for comparing the electrocardiogram waveform data with the standard data, a determination unit for determining one of presence and absence of abnormality according to whether a difference between the electrocardiogram waveform data and the standard data exceeds a permissible range, and an alarm generator for raising an alarm when the determination unit determines the presence of abnormality.

2 Claims, 1 Drawing Sheet

PORTABLE ELECTROCARDIOGRAM MONITOR

CROSS-REFERENCE TO RELATED APPLICATIONS

This application is based upon and claims the benefit of priority from the prior Japanese Patent Applications No. 11-152472, filed May 31, 1999; and No. 2000-134704, filed May 8, 2000, the entire contents of which are incorporated herein by reference.

BACKGROUND OF THE INVENTION

The present invention relates to a portable electrocardiogram monitor which can easily be carried with a user having a heart disease as a chronic one while he or she is traveling or the like.

Various types of portable medical equipment have recently been developed in accordance with a transition to an aging society; however, no portable electrocardiogram monitors have been done yet. Electrocardiograms are tracing made by inducing bioelectric currents generated by the contraction of heart muscles. It is thus difficult for an amateur having no expert knowledge to find heart abnormalities at a glance at the electrocardiogram.

As described above, high-level expert knowledge is required in order to determine by electrocardiograms whether a heart is normal or abnormal. So far no home-based portable electrocardiogram monitors have been spread widely.

BRIEF SUMMARY OF THE INVENTION

The object of the present invention is to provide a portable electrocardiogram monitor capable of accurately checking whether a user's heart is normal or not by a simple operation without any expert knowledge.

In order to attain the above object, a portable electrocardiogram monitor of the present invention has the following features in structure.

(1) A portable electrocardiogram monitor according to the present invention comprises:
  an electrode piece fixed in contact with a surface of a body of a user, for receiving an electrical signal corresponding to a bioelectric current generated by contraction of heart muscles;
  a signal amplifier for amplifying the electrical signal received by the electrode piece;
  a processor for processing a signal amplified by the signal amplifier to acquire electrocardiogram waveform data;
  a display for displaying an electrocardiogram based on the electrocardiogram waveform data acquired by the processor;
  a memory for storing electrocardiogram waveform data of the user who is in good health, as standard data;
  a comparator for comparing the electrocardiogram waveform data acquired by the processor with the standard data stored in the memory;
  a determination unit for determining one of presence and absence of abnormality according to whether a difference between the electrocardiogram waveform data and the standard data, compared by the comparator, exceeds a permissible range; and
  an alarm generator for raising an alarm when the determination unit determines the presence of abnormality.

(2) The portable electrocardiogram monitor described in above item (1), wherein the standard data is average electrocardiogram waveform data of the user who is in good health, processed by the processor for preparation of measurement and stored in the memory in advance.

(3) The portable electrocardiogram monitor described in item (1), wherein the alarm generator includes at least one of acoustic alarm generation means using sound, optical alarm generation means using light, and information-transmission type alarm generation means using character information and image information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION (Embodiment)
[Structure]

Figure 1:
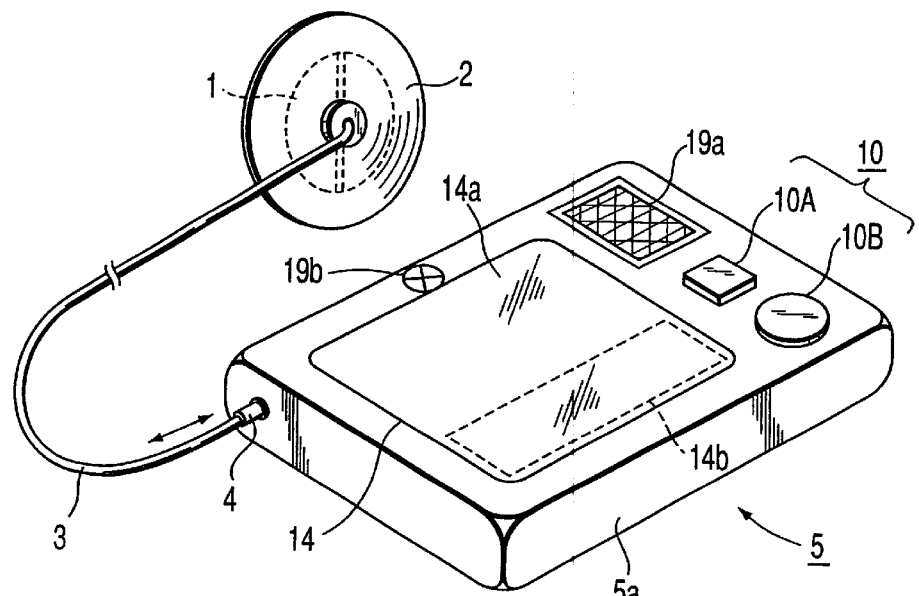
FIG. 1 is a perspective view of the outward appearance of a portable electrocardiogram monitor according to one embodiment of the present invention.

In FIG. 1, reference numeral 1 indicates an electrode piece fixed in contact with the surface of a user's body, such as a chest, for receiving electrical signals corresponding to bioelectric currents generated by the contraction of heart muscles, and numeral 2 denotes a vacuum-type adsorption disk formed so as to surround the electrode piece 1 and used for fixing the piece 1 in contact with the surface of a user's body. The electrode piece 1 is connected to one end of a connection cable 3. An attachment plug 4 is attached to the other end of the cable 3 such that the cable 3 is detachably connected to a monitor body 5 as indicated by a double-headed arrow.

The monitor body 5 includes a case 5a which is made so compact that it can easily be carried with a user, and the case 5a is equipped with various constituting elements as will be described later. The top surface of the case 5a is mounted with an operation switch 10 having buttons 10A and 10B, a display 14 having a display screen (areas 14a and 14b), an alarm buzzer 19a, and an alarm lamp 19b. The operation switch 10 and the display 14 will be described later.

Figure 2:
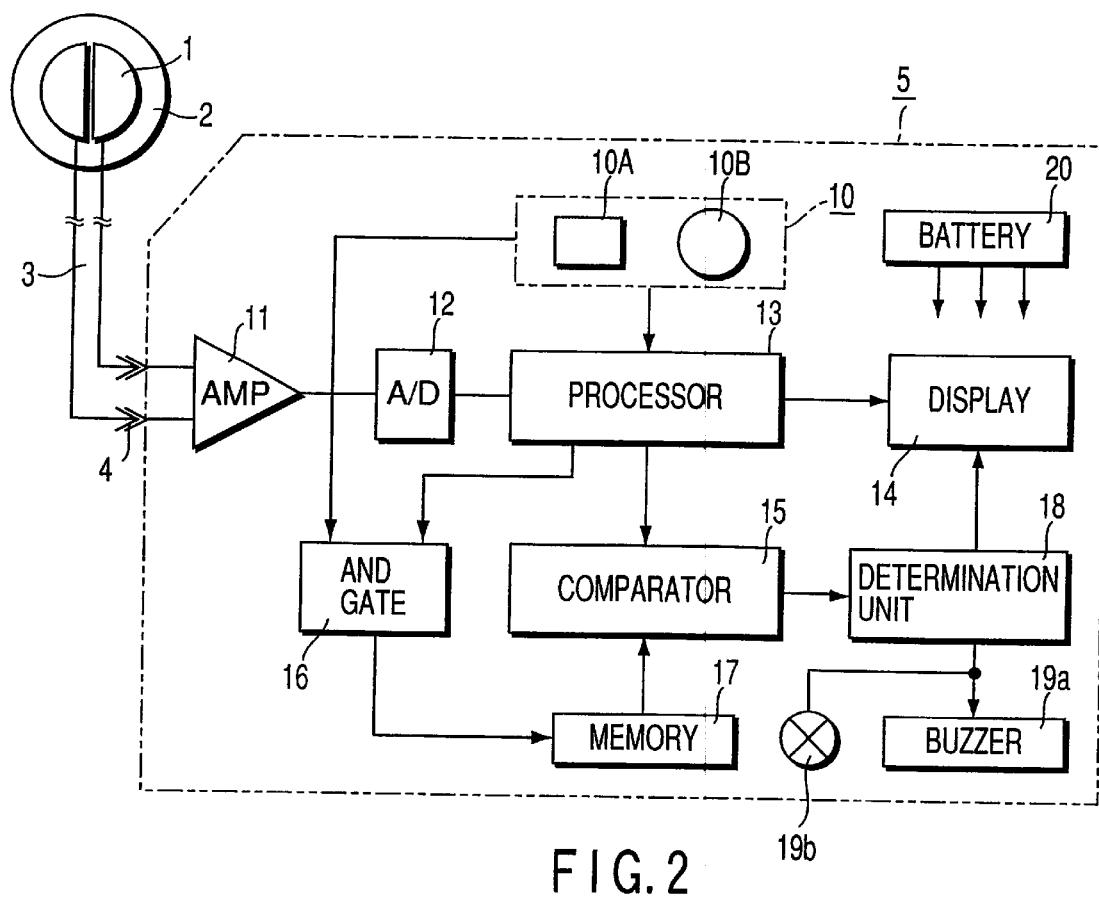
FIG. 2 is a block diagram of the structure of the portable electrocardiogram monitor according to the embodiment of the present invention.

Referring to FIG. 2, the monitor body 5 contains a signal amplifier 11, an A/D converter 12, a processor 13, a comparator 15, an AND gate 16, a memory 17, a determination unit 18, and a battery 20 as electronic components operating in response to a button operation of the operation switch 10.

The signal amplifier 11 amplifies the electrical signal received by the electrode piece 1. The amplified signal is converted to a digital signal by the A/D converter 12 and the digital signal is input to the processor 13. The processor 13 processes the digital signal to generate electrocardiogram waveform data and then supply it to both the display 14 and comparator 15.

The processor 13 receives an instruction from the operation switch 10 and supplies the display 14 with a content corresponding to the instruction. Usually the display 14 oscillographically displays an electrocardiogram in the area 14a of the display screen based on the electrocardiogram waveform data from the processor 13.

The AND gate 16 turns on in response to an ON command signal given from the operation switch 10 in the measurement preparatory stage to store electrocardiogram waveform data of the user who is in good health, which is acquired by the processor 13, in the memory 17 as standard data. The memory 17 thus stores the standard data.

The comparator 15 compares the electrocardiogram waveform data supplied from the processor 13 with the standard data stored in the memory 17 and sends a difference between them to the determination unit 18. The determination unit 18 determines the presence or absence of abnormality according to whether the difference exceeds a fixed permissible range. If the unit 18 determines that abnormality is present, it supplies abnormality information to the display 14 as well as the alarm buzzer 19a and alarm lamp 19b.

Upon receiving the abnormality information from the determination unit 18, the alarm buzzer 19a issues an audible alarm continuously or intermittently. The alarm lamp 19b is blinking red to raise an alarm. The display 14 displays the abnormality in the area 14b of the display screen as a message. The alarm buzzer 19a, alarm lamp 19b, and a message display section of the display 14 constitute an alarm generator. The alarm generator includes an acoustic alarm generation means using sound, an optical alarm generation means using light, and an information-transmission type alarm generation means using character information and image information.

The battery 20 is constituted of a dry cell or a chargeable battery pack to supply power to the respective elements of the monitor body 5.

[Operation]

An operation of the portable electrocardiogram monitor having the above structure will now be described.

First an operation of storing electrocardiogram waveform data of a user, which is measured in advance when he or she is in good health, in the memory 17 as standard data, will be described.

When a user is in good health, the electrode piece 1 is fixed to part of the chest, which is as close to the heart as possible, using the adsorption disk 2. If, in this state, the button 10A of the operation switch 10 for a preparatory mode is turned on, then the AND gate 16 is turned on by the battery 20 and the monitor is set in the preparatory mode. An electrical signal corresponding to a bioelectric current is input to the electrode piece 1 and amplified by the signal amplifier 11. The amplified signal is converted to a digital signal by the A/D converter 12. The digital signal is supplied to the processor 13 and processed as electrocardiogram waveform data. The electrocardiogram waveform data is sent to and stored in the memory 17 through the AND gate 16 which has already turned on. It is desirable to calculate the average of data for two and three minutes in order to store the standard data.

Next a measurement operation will be described. If the button 10B of the operation switch 10 for a measurement mode turns on when the above standard data is stored in the memory 17, the AND gate 16 turns off and the monitor is set in the measurement mode. In this mode, on one hand, electrocardiogram waveform data generated from the processor 13 is supplied to the display 14 and displayed in the area 14a of the display screen as an electrocardiogram; on the other hand, it is supplied to one input terminal of the comparator 15. The standard data is transmitted to the other input terminal thereof from the memory 17. The comparator 15 compares the electrocardiogram waveform data generated from the processor 13 with the standard data stored in the memory 17 and detects a difference between them. The detected difference is sent to the determination unit 18. The unit 18 determines the presence or absence of abnormality according to whether the difference exceeds a fixed permissible range.

When the determination unit 18 determines that abnormality is present, it issues an abnormality signal and supplies it to the alarm buzzer 19a, alarm lamp 19b, and display 14. The alarm buzzer 19a raises an audible alarm and the alarm lamp 19b is blinking red to notify the user of the abnormality. The abnormality is displayed in the area 14b of the display screen of the display 14 as a message.

When abnormality is detected in the heart of a user or when the measured electrocardiogram data greatly deviates from the standard data, the alarm is automatically given to the user. For this reason, even though the user has no expert knowledge about electrocardiogram waveforms, he or she can correctly understand whether the heart is normal or abnormal.

In the portable electrocardiogram monitor according to the embodiment of the present invention, normal electrocardiogram data of a user who is in good health is used as standard data, and the presence or absence of abnormality is determined according to whether a difference between the current and usual conditions exceeds a fixed value by comparing the measured electrocardiogram waveform data with the standard data. Therefore, a considerably more accurate determination result can be expected, without causing a major error in determination of abnormality, though a complicated, sophisticated scientific analysis or determination technology is not adopted.

(Modifications)

The portable electrocardiogram monitor according to the embodiment of the present invention can be modified as follows:

1) The alarm buzzer can be replaced with a speaker for making an announcement according to the alarm; and 2) The monitor body 5 can be mounted with a fixing band, a strap suitable for carrying the monitor, or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A portable electrocardiogram monitor comprising:

an electrode piece fixedly contacting a surface of a body of a user, for receiving an electrical signal corresponding to bioelectric current generated by contraction of heart muscles;

a signal amplifier for amplifying the electrical signal received by the electrode piece;

a processor for processing a signal amplified by the signal amplifier to acquire electrocardiogram waveform data;

a display for displaying an electrocardiogram based on the electrocardiogram waveform data acquired by the processor;

a reference data storing memory for storing reference data of the electrocardiogram waveform data;

a comparator for comparing the electrocardiogram waveform data acquired by the processor with the reference data stored in the reference data storing memory;

a determination unit for determining one of presence and absence of abnormality according to whether a difference between the electrocardiogram waveform data and the reference data, compared by the comparator, exceeds a permissible range;

an alarm generator for raising an alarm when the determination unit determines the presence of abnormality;

an operation switch having a preparatory mode button which turns on in a measurement preparatory stage and a measurement mode button which turns on during measurement; and reference data storing means including a gate which turns on when the preparatory mode button of the operation switch turns on, said reference data storing means supplying the electrocardiogram waveform data processed by the processor to the reference data storing memory through the gate and storing the electrocardiogram waveform data in the reference data storing memory as reference data.

2. The portable electrocardiogram monitor according to claim 1, wherein the alarm generator includes at least one of acoustic alarm generation means using sound, optical alarm generation means light, and information-transmission type alarm generation means using character information and image information.

* * * * *